United States Patent [19]

Marion

[11] 4,443,214
[45] Apr. 17, 1984

[54] VALVE FOR THE TREATMENT OF HYDROCEPHALUS

[75] Inventor: Bernard Marion, Montreuil sur Ille, France

[73] Assignee: Society dite: sophysa, Montreuil sur Ille, France

[21] Appl. No.: 346,193

[22] Filed: Feb. 5, 1982

[30] Foreign Application Priority Data

Mar. 18, 1981 [FR] France ............................... 81 05389

[51] Int. Cl.³ .............................................. A61B 5/00
[52] U.S. Cl. .......................................... 604/9; 604/10
[58] Field of Search ...................................... 604/8–10, 604/247; 137/539; 251/65

[56] References Cited

U.S. PATENT DOCUMENTS 3,886,948  6/1975  Hakim ....................................... 604/9
4,156,422  5/1979  Hildebrandt et al. ................... 604/9

*Primary Examiner*—C. Fred Rosenbaum
*Assistant Examiner*—Sherri E. Vinyard
*Attorney, Agent, or Firm*—Karl F. Ross; Herbert Dubno

[57] ABSTRACT

This valve adapted to be inserted between a ventricular catheter and a draining catheter comprises a body of flattened cylindrical shape enclosing a chamber having formed through its cylindrical wall an inlet passage for introducing the cephalorachidian fluid and an outlet passage for discharging this fluid. At the inner end of the inlet passage a frustoconical seat engageable by a ball valve acting as a non-return valve is provided, this ball valve being urged against the seat by a curved spring blade extending along the lateral inner wall of the chamber and mounted preferably in overhanging relationship on a diameter bar of magnetic material mounted in turn for concentric rotation on a pivot pin extending across the chamber. A tooth carried by the bar end opposite the spring blade is adapted to engage detent-positioning dents formed in the lateral wall of the chamber.

5 Claims, 2 Drawing Figures

VALVE FOR THE TREATMENT OF HYDROCEPHALUS

BACKGROUND OF THE INVENTION

1. Field of the Invention

The present invention relates to a valve for the treatment of hydrocephalus.

It is known that hydrocephalous is a disease caused notably by an abnormal accumulation of cephalo-rachidian or cerebrospinal fluid in the cavities (ventricles) of the brain, and more particularly by the clogging of the natural loculi (usually referred to as arachnoid villosities) for the resorption of the cephalo-rachidian fluid. This clogging is attended by a volumetric increment of the ventricles of the cranial cavity of brain-pan and consequently of the skull itself in newborn children having still open fontanelles.

In adults, due to the rigidity of the brain-pan, this disease is revealed by disorders affecting the locomotive organs, by incontinences, mental disorders and/or a gradual deterioration of the cerabral parenchyma.

One known method of treating this disease consists in diverting the cephalo-rachidian fluid contained in the ventricles of the cranial cavity towards any other resorption region such as the heart or the peritoneum.

For this purpose, a catheter is introduced into one of the ventricles of the brain-pan by trepanning the patient's skull, this catheter being subsequently connected to another tube inserted under the scalp and leading at the neck level either to the jugular vein (in which case the apparatus is completed by introducing a distal catheter into the left-hand auricle) or simply to the peritoneum.

Therefore, the assembly comprises an upstream catheter and a downstream catheter, but in fact it constitutes a unitary system which must be connected once or twice, according to the particular model utilized. The shunt assembly, from its proximal end to its distal end, is completely sub-cutaneous, thus affording a certain freedoom of movement to the patient and avoiding infections.

The arachnoid villosities keep a constant pressure between the cephalo-rachidian fluid and the venous blood. Furthermore, they prevent the ventricles of the brain-pan from being drained off in the orthostatic position.

Consequently, when a system for diverting the cephalo-rachidian or cerebro-spinal fluid is grafted to a patient, an adequate valve system must be inserted therein. This valve is disposed either at the end of the system and is therefore a distal valve disposed near the trepan orifice, and in this case the valve is referred to as a proximal one.

2. The Prior Art

A number of valve types have already been proposed up to now for such shunting systems utilized in the treatment of hydrocephalus.

Among these known valves, those invented by Pudenz, Raimondi and Holter are of the slotted type and are simply formed in the wall of the tube consisting of silicone elastomer, the valve slots opening when the cephalo-rachidian fluid attains a predetermined pressure.

The Pudenz and Raimondi valves comprise slots formed at the distal, closed end of the circuit.

The Holter valve comprises a tubular sheath adapted to be positionned in the vicinity of the trepan orifice. In the sheath ends small cupula of a silicone base material are introduced and have lateral slots formed therein to permit the flow of cephalo-rachidian fluid therethrough.

Also known in the art is the Hakim valve which comprises a mechanical device for controlling the fluid pressure.

This device consists of a ball valve cooperating with a frustoconical seat; this ball valve is urged to its seated position by a gaged spring so that the valve will open under a predetermined pressure. One advantage of this Hakim valve over slotted valves is that it opens under a precision-gaged pressure.

However, whatever the precision of operation of these known valves, they are objectionable in that they are capable of operating in only one pressure range, so that a complete series of valves must be provided for operating in different pressure ranges consistent with the various cases of hydrocephalus to be treated.

Moreover, it may be expected that during the evolution of the disease or during its treatment the valve ingrafted initially will open under an excessive high or low pressure.

In this case the valve must be replaced and this involves of course another surgical operation.

OBJECT OF THE INVENTION

It is the primary object of the present invention to avoid the inconveniences characterizing the valves of the prior art by providing a valve which combines the advantages of a good degree of precision with the possibility of adjusting them from the outside at several pressure values without resorting to any surgical operation for removing and re-grafting the valve.

Several types of adjustable valves have already been proposed, such as the one disclosed in the French Pat. No. 2.354.103 filed by Messerschmitt-Bolkow-Blohm G.m.b.H on June 9, 1977. This valve intended for grafting between the scalp and the brain-pan, is adapted to regulate the pressure of the cephalo-rachidian fluid delivered to a chamber bounded by a membrane engaged by a lever adapted to actuate a valve inserted in the discharge drain.

In the device, the membrane deformation and therefore the position of the valve control lever are responsive to a feeler provided with a gaged spring adjustable by rotating a screw-and-nut assembly in the proper direction.

Considering the fact that a valve for the purpose set forth hereinabove must be extremely simple, light and reliable, it is obvious that the valve proposed by Messerschmitt et al. does not meet this requirement.

In all known valves intended for this specific purpose and comprising a spring as in the device proposed by Hakim, this spring is a coil compression spring. However, the U.S. Pat. No. 4,072,167 delivered on Feb. 7, 1978, to Caterpillar Tractor Co. discloses a valve of which the movable member (a ball) is urged to its seated position by a torsion spring exerting a force varying with the angular position of its fixed end. This valve-contemplated primarily for regulating hydraulic circuits-can operate only under relatively high fluid pressures, namely the pressures whereat conventional coil compression springs become inoperative, as clearly acknowledged in the patent specification.

SUMMARY OF THE INVENTION

The above-defined problem is solved by the present invention through the provision of completely different structures having the additional advantage of miniaturizing the instrument. Its only common feature with the Messerschmitt valve is that it comprises likewise magnetic adjustment means.

The subcutaneous valve of this invention for the treatment of hydrocephalous is adapted to be inserted and branched between a ventricular catheter and a draining catheter, comprises a body forming a flat cylindrical chamber, a feed passage for introducing the cephalo-rachidian fluid into the valve body having a non-retourn valve, for example a ball valve, inserted in its outlet passage and responsive to a spring of which the force is adjustable by means of external control means, and a tube for discharging said fluid, and is characterized in that feed passage opens into said flat cylindrical chamber through a port formed in the cylindrical wall of the chamber, a curved spring blade constantly urging said valve towards its seat with a force adjustable by means of a movable member.

Only spring blades can be utilized with the valve of this invention, since they are the only ones having the requisite sensitivity.

Other features of the invention will appear from the following description of a typical form of embodiment of the invention, given by way of example, not of limitation, and illustrated in the attached drawing.

DESCRIPTION OF THE PREFERRED EMBODIMENT

Figure 1:
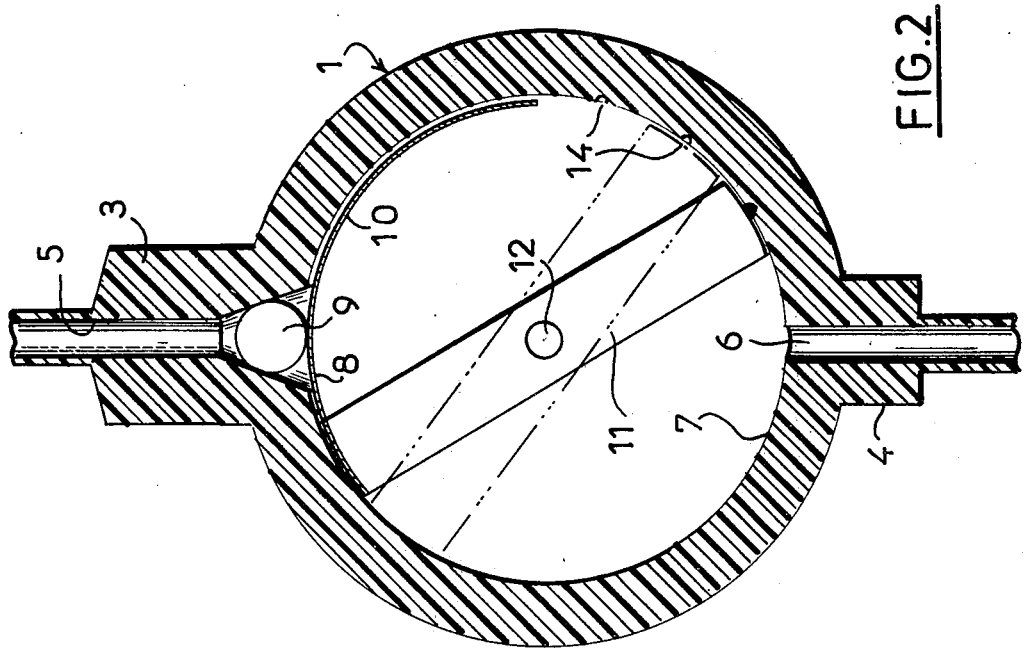
FIG. 1 is an axial section of a valve according to this invention, shown in the position of minimal flow pressure of the cephalo-rachidian fluid.

The valve illustrated in FIG. 1 comprises essentially a valve body 1 of flat cylindrical form, made of a suitable plastic material.

Formed on this valve body 1 are two diametrally opposed projections 3 and 4 in which an inlet passage 5 and an outlet passage 6 for the cephalo-rachidian fluid are formed, respectively. These passages 5 and 6 open into the lateral cylindrical inner wall of a chamber 7 of a shape corresponding to that of said cylindrical body 1.

At the inner end of the fluid inlet passage 5 a frusto-conical valve seat 8 is provided for engagement by a corresponding ball valve 9. If desired, this seat 8 may be adjustable in its axial direction.

The ball valve 9 is normally urged against its seat 8 by a curved spring blade 10 extending along one portion of the lateral cylindrical inner wall of chamber 7. This spring 10 may advantageously extend over one-fourth of the circumference of said chamber 7.

In the form of embodiment illustrated in the drawing this curved spring 10 is fastened at one end, consequently in overhanging relationship, to one end of a diametral rotor-forming bar 11 of magnetic material, adapted to rotate concentrically in chamber 7 about a pivot pin 12. The spring 10 is slightly shorter than the diameter of chamber 7.

At its end opposite the spring 10 the bar 11 is provided with a small tooth 13 adapted to penetrate corresponding dents 14 formed in the inner cylindrical wall of the chamber for detent positioning the rotor-forming bar 11 in anyone of the angular positions corresponding to as many operating pressures of the valve.

In the position of bar 11 shown in FIG. 1, it will be seen that the point of contact between spring blade 10 and ball valve 9 is relatively remote from the fastening point of blade 10 on bar 11, so that the resistant moment of the spring, which counteracts a thrust exerted by the fluid on ball valve 9, is relatively weak.

As a result, the ball valve 9 can be unseated by a relatively low pressure exerted by the cephalo-rachidian fluid flowing through the passage 5.

Figure 2:
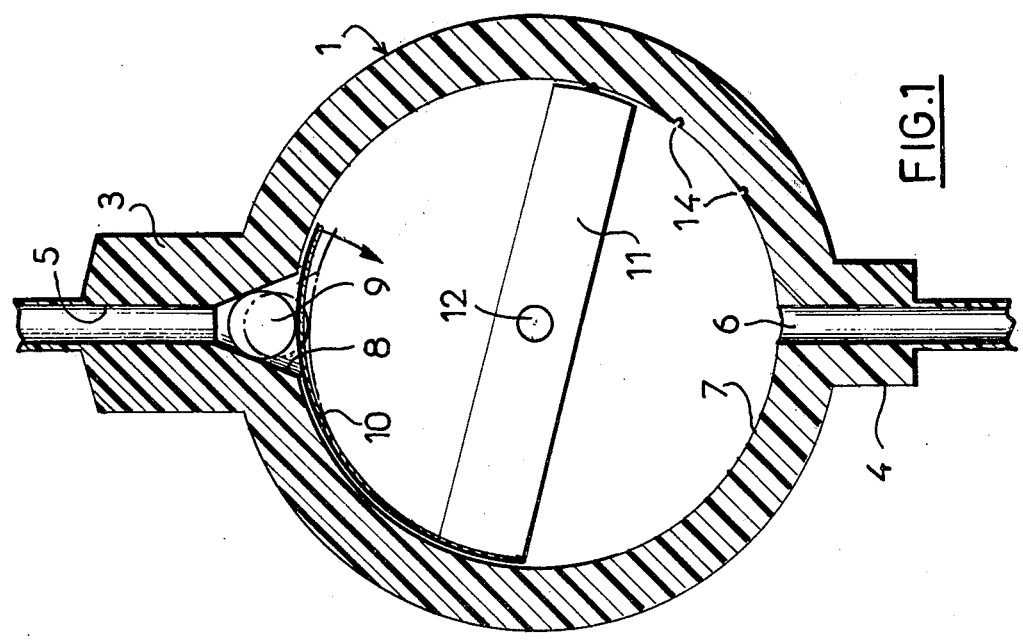
FIG. 2 is a view similar to FIG. 1, but showing the valve gaged for a maximal operating pressure.

In contrast thereto, in the position of bar 11 shown in FIG. 2, the point of contact between spring blade 10 and ball valve 9 is relatively close to the fastening point of blade 10, so that the spring resistance to the fluid pressure is considerably higher and corresponds to the maximal operating pressure of the device.

It is obvious that a single spring blade is sufficient for producing the two pressure values; however, the difference between these two values is relatively small, in comparison with the angular difference between the two positions of bar 11, which is relatively great.

If we compare the mode of operation of the valve of the present invention with the valve disclosed in the Messerschmitt et al. patent, it appears that in the latter the change in pressure is hardly perceptible visually and requires the use of an inductive displacement sensor.

It is on the other hand unnecessary to add a Figure to the drawing for understanding that the spring 10, instead of being movable bodily with the diametral bar 11, may also be secured at one end to the valve body 1.

In this case, the magnitude of the spring resistant moment is determined by the position of the adjacent end of bar 11 engaging the innner face of spring 10.

The cephalo-rachidian fluid flows from the inlet passage 5 to the outlet passage 6 on either side of the rotor-forming bar 11 of which the thickness is about one-half the height of the internal chamber 7.

To each dent 14 formed in the lateral wall of chamber 7 there corresponds a different position of the point of contact between spring blade 10 and ball valve 9 and therefore a different valve operating pressure.

Of course, the device shown in the drawing is coated with, or embedded in, a protective material consistent with the human tissues, for example, a suitable silicone elastomer (not shown). This device is connected on the one hand to a conventional upstream drain coupled to a ventricular catheter, and on the other hand to a distal downstream drain or draining catheter.

Since the rotor-forming bar 11 consists of a piece of magnetic material, it can be rotated from outside by means of a magnet (not shown) acting through the valve wall and the cutaneous tissues covering this valve when the latter is grafted in the desired position in the patient's body.

Thus, the valve closing pressure can be remote-controlled by the neurosurgeon without involving any mechanical contact with the device, so that it is unnecessary to make an incision in the patient's body.

Moreover, the above-described valve is programmable and dispenses with the use of several valves operating under different pressures during the evolution of the disease.

What is claimed as new is:

1. A subcutaeneous valve for the treatment of hydrocephalus adapted to be inserted between a ventricular catheter and a draining catheter, said valves comprising:
- a valve body formed with a cylindrical chamber having a cylindrical wall;
- an inlet formed in said wall and connectable to said ventricular catheter, an outlet formed in said wall opening into said chamber and connectable to said draining catheter;
- means forming a valve seat at said inlet;
- a valve member juxtaposed with said valve seat and engageable therewith to block flow from said chamber to said ventricular catheter but displaceable away from said valve seat to permit flow from said ventricular catheter into said chamber;
- a rotor journaled in said chamber for rotation about the axis of said chamber and having a portion reaching toward said wall of said chamber, said rotor being provided with means magnetically couplable with an actuator externally of said body for magnetic rotation of said rotor in said chamber;
- a spring blade fixed to said portion of said rotor, extending arcuately along said wall, bearing deflectably outwardly against said member and sliding thereon to bias said member against said seat with a force which is a function of the angular position of said rotor in said chamber; and
- indexing means between said rotor and said wall for indexing said rotor in a selected one of a plurality of angular positions upon rotation of said rotor by magnetic coupling thereto.

2. The valve defined in claim 1 wherein said rotor is a bar extending diametrically in said chamber and having one end secured to said spring.

3. The valve defined in claim 2 wherein said valve member is a ball and said spring extends along at least one quarter of the periphery of said chamber.

4. The valve defined in claim 1 wherein said indexing means includes a detent carried by said rotor, said wall having a plurality of spaced-apart indentations for selectively receiving said detent, thereby setting the member to react to a respective predetermined opening pressure at said ventricular catheter.

5. The valve defined in claim 1 wherein said spring blade has a free end biased against said member.

* * * * *